United States Patent [19]
Koscher et al.

[11] Patent Number: 5,810,865
[45] Date of Patent: Sep. 22, 1998

[54] SURGICAL INSTRUMENT

[76] Inventors: Stefan Koscher, Lachstrasse 53; Johann Würtz, Semmelweiss-Strasse 32, both of D-78549 Spaichingen, Germany

[21] Appl. No.: 809,064

[22] PCT Filed: Sep. 14, 1995

[86] PCT No.: PCT/EP95/03622

§ 371 Date: Jul. 2, 1997

§ 102(e) Date: Jul. 2, 1997

[87] PCT Pub. No.: WO96/09008

PCT Pub. Date: Mar. 28, 1996

[30] Foreign Application Priority Data

Sep. 20, 1994 [DE] Germany .......................... 44 33 403.6
Jan. 21, 1995 [DE] Germany ....................... 195 01 752.8

[51] Int. Cl.$^6$ ................................................. A61B 17/28
[52] U.S. Cl. ................... 606/174; 606/205; 606/207; 606/208; 30/341
[58] Field of Search .............................. 30/260, 335, 337, 30/340, 341; 606/167, 174, 175, 205, 206, 207, 208

[56] References Cited

U.S. PATENT DOCUMENTS

| 1,577,880 | 3/1926 | Stuart | 279/93 |
| 2,069,636 | 2/1937 | Wilson | 30/260 |
| 2,725,629 | 12/1955 | Todhunter | 30/260 |

FOREIGN PATENT DOCUMENTS

| 3509212 | 10/1985 | Germany . |
| 243732 | 2/1947 | Switzerland . |
| 1441608 | 7/1976 | United Kingdom . |

*Primary Examiner*—Michael Buiz
*Assistant Examiner*—David O. Reip
*Attorney, Agent, or Firm*—Bachman & LaPointe, P.C.

[57] ABSTRACT

In a surgical instrument having at least one jaw part (6, 7) which is turnable around a pin (11), the jaw part (6, 7) is connected via a receiver (8, 9) with the pin (11), and the jaw part (6, 7) is detachably fastened with respect to the receiver (8, 9).

22 Claims, 4 Drawing Sheets

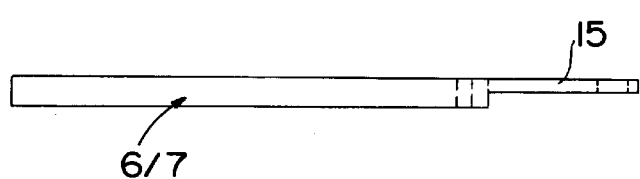
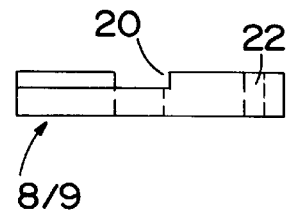
FIG. 4   FIG. 5
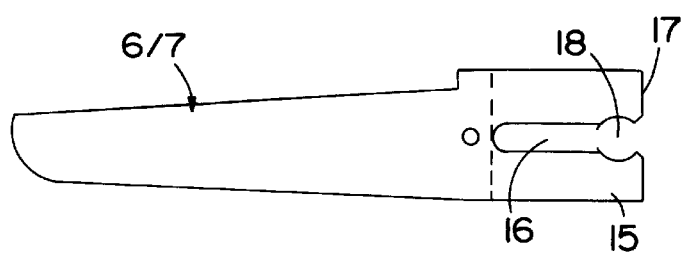
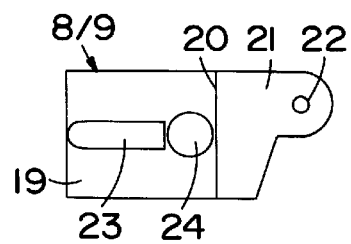
FIG. 6   FIG. 7
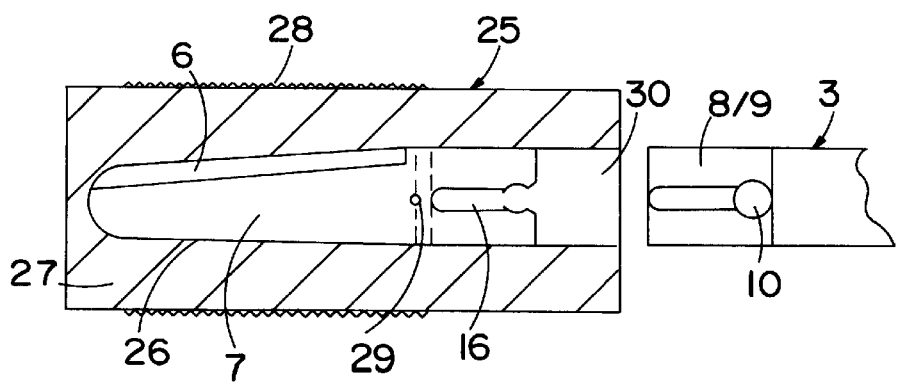
FIG. 8

SURGICAL INSTRUMENT

BACKGROUND OF THE INVENTION

The present invention relates to a surgical instrument having at least one jaw part which is rotatable around an axis.

Such surgical instruments are known and available on the market in many forms and embodiments. The corresponding jaw parts can serve for cutting, clamping, twisting-off, shearing, or the like. As a rule, they serve for performing given surgical interventions in man or animal. These instruments and their development have increased considerably in importance, as a result in particular of endoscopy.

As example, reference is had here to a surgical instrument in accordance with P 43 32 497.5.

In all of these instruments, the jaw parts are connected by a corresponding pull or push element with actuating members, for instance scissor arms. Upon actuation of the scissor arms, the jaw parts are opened and closed. In this connection, either both jaw parts can be movable or one jaw part can be stationary and the other jaw part moved. As soon as the jaw parts are worn out, the instrument is thrown away.

There are also available on the market disposable instruments which are intended only for one operation and are then discarded. These disposable instruments are supplied in sterile packings, so that the disposing of the packing and of the instrument itself represents a considerable expense and is very problematic based on environmental considerations.

The object of the present invention is to provide a surgical instrument which can be repeatedly reused and in which wear of the jaw parts does not constitute a problem. Furthermore, the possibility of sterilizing the instrument is to be facilitated.

In order to achieve this object, the jaw part is connected via a receiver to the pin and the jaw part is detachably fastened with respect to the receiver.

The basic concept of the present invention is that, particularly when worn, the jaw part can be detached from the receiver and be replaced by a new jaw part. In this way, the rest of the surgical instrument is fully retained and can be sterilized and repeatedly reused. Since the jaw part constitutes only an extremely slight portion of the manufacture work and cost of the surgical instrument, the present invention results in a substantial reduction of the cost, particularly in hospitals.

As jaw part, a large number of embodiments can enter into consideration. It need merely be seen to it that the action of the jaw parts does not conflict with their detachable connection. In other words, the jaw part should not carry out any activity in which a strong pull is exerted on the jaw parts. In particular, there enters into consideration a development of the jaw parts as scissor blades, as well as jaw parts which are used today in biopsy forceps.

The rest of the instrument is preferably so designed that it can easily be sterilized. For this, a surgical instrument in accordance with P 43 32 497.5 offers itself.

After detachment from the receiver, the jaw parts can either be thrown away and replaced by new ones, or they can be sterilized and/or reworked. A dull scissor blade can, for instance, be ground fresh and used again. Thus, the invention contributes considerably to reducing waste, in which connection, furthermore, only a slight amount of packing is necessary for the surgical instrument and the jaw parts. Of course, it is also possible to use on the same instrument different jaw parts with which different activities can be carried out.

In a preferred embodiment, the jaw part has an extension with a guide slot which cooperates with a guide arm on a support plate of the receiver. This guide arm effects a targeted fastening of the jaw part to the receiver or a corresponding detent element. Therefore, there should also be provided on the receiver, in addition, a shoulder against which the jaw part strikes for the limiting of its motion.

For the fastening by detent of the jaw part with respect to the receiver, it is preferred to provide in the region of the guide slot a detent hole which cooperates with a detent element. This detent element can be provided separately on the receiver, as a result of which, to be sure, the total length of the jaw is increased by about 3 mm. Since this is not always desirable, it is possible to use the above-mentioned pin also as detent element. In other words, the jaw part, guided by the guide arm in the guide slot, is pushed so far along the receiver that the guide slot strikes against the pin. By briefly pressing on the jaw part, the pin then slides into the detent hole, the guide slot opening somewhat for a short time.

The receiver itself then has, on the other side of a hole for the pin, a nose extension which is articulated via a spread lever to a pull or push element. This pull or push element effects the rotation of the receiver, and thus of the jaw part, around the pin.

In another embodiment, an elastic element which in position of use engages behind at least one undercut, an edge, or the like in or on the receiver is arranged on the jaw part and/or the receiver.

This engagement by the elastic element means that a loosening of the jaw part from the receiver can only take place when the elastic element has been deflected in such a manner that it no longer engages behind the undercut, regardless of the nature thereof. This also means, however, that some expedient must be provided in order to effect a deflection of the elastic element. In this way, the reliability of the fastening of the jaw part on the receiver is assured and, in particular, the operator need no longer fear that a jaw part will become detached from the receiver during an operation in the human body and that can be removed from the body again only with great difficulty, for instance in the case of endoscopic interventions.

For the reliable detachable fastening of the jaw part on the receiver, there are many possibilities. In this connection, it is immaterial whether the elastic element be present on the jaw part or on the receiver. The inventive concept always covers in all cases also the reverse arrangement. The following description of two embodiments is therefore merely illustrative.

In the first embodiment, the jaw part has an extension with which there is associated an elastic tongue having a detent nose. From a purely manufacturing standpoint, this tongue can be suitably produced by stamping. In this connection, a suitable tongue can remain in a guide slit or else in a C-shaped slot.

It is essential that the detent nose engage behind an undercut and at the same time become free from this undercut by deflection of the tongue. In order to facilitate this, the elastic tongue should have a tapered region which facilitates the deflection.

As undercut, there can be used any projection or, in particular, also slot in the receiver, into which the detent nose snaps. In this case, it is desirable that, upon the insertion of the jaw part into the receiver, the jaw part be guided so that the detent nose also reaches the corresponding undercut. For this purpose, corresponding guide arms on the receiver serve, they cooperating, for instance, with guide slots. However, the same purpose is served also by a simple trough-shaped development which is formed at the end on the jaw part or a corresponding extension on the jaw part. This development seeks a congruent projection on the receiver.

In another embodiment of the invention, the elastic element consists essentially of a detent strip which snaps behind an edge of the guide arm on the receiver. The guide arm preferably also has grooves on both sides into which arms which extend into the opening of a step-wise recess are guided. In this connection, on the one hand, the object is satisfied that the jaw part is guided upon the connecting with the receiver while, on the other hand, the advantage is also obtained that the jaw part cannot be loosened from the receiver even if it is bent-off laterally from the receiver. The arms in the grooves prevent the lateral breaking-out of the jaw part, so that a placing of this jaw part on a receiver from the outside is also possible.

Particular attention is to be paid to the fact that the detachable fastening of the jaw part is effected in such a manner that the jaw part does not unintentionally loosen from the rest of the surgical instrument, for instance in the body of a patient. In other words, detent hole and pin must be so adapted to each other that while the pushing-on of the jaw part is possible, nevertheless a pulling-off of the jaw part can take place only under difficult conditions. Therefore, in a preferred embodiment of the invention, a mounting adapter is provided which permits better access to and better handling of the jaw parts. The jaw parts are so arranged in the mounting adapter that they cannot be shifted. At the same time, however, there is an opening in the mounting adapter into which the front part of the surgical instrument without the jaw parts can be introduced. Since in this case, the mounting adapter permits a greater pressure upon the clipping of the jaw parts onto the pin, the diameter of the detent hole can, for instance, be made somewhat smaller or else the thickness of the extension having the detent hole can be increased. This is so adapted that the pulling-off of the jaw parts with only two fingers is no longer possible.

Of course, many possibilities which lie within the scope of the present invention are conceivable for a mounting adapter.

BRIEF DESCRIPTION OF THE DRAWINGS

Further advantages, features, and details of the invention will become evident from the following description of preferred embodiments and from the drawing, in which:

FIG. 4 is a side view of a scissor blade in accordance with the invention;

FIG. 5 is a side view of a scissor-blade receiver in accordance with the invention;

FIG. 6 is a top view of the scissor blade of FIG. 4;

FIG. 7 is a top view of the scissor-blade receiver of FIG. 5;

FIG. 8 is a longitudinal section through a mounting adapter in accordance with the invention, with scissor blades inserted, and of a front part of the surgical instrument;

DETAILED DESCRIPTION

Figure 1:
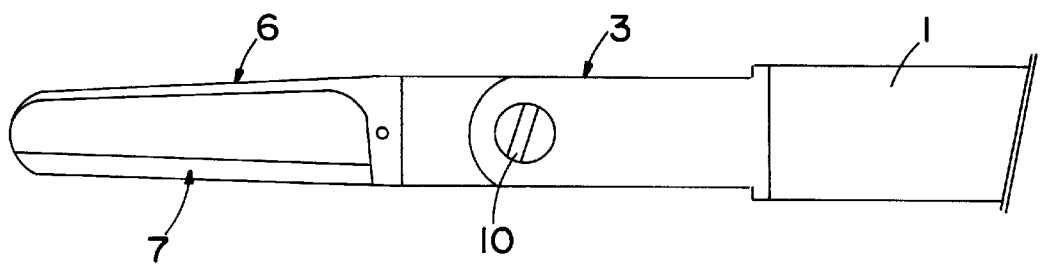
FIG. 1 is a top view of a front part of a surgical instrument.
Figure 2:
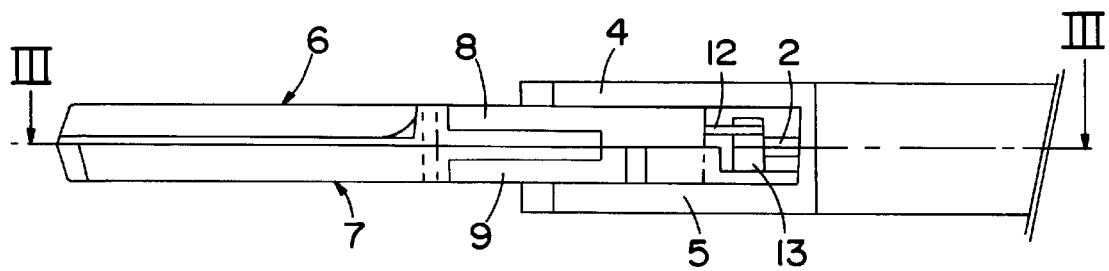
FIG. 2 is a top view on the front part of the surgical instrument of FIG. 1, turned 90°.
Figure 3:
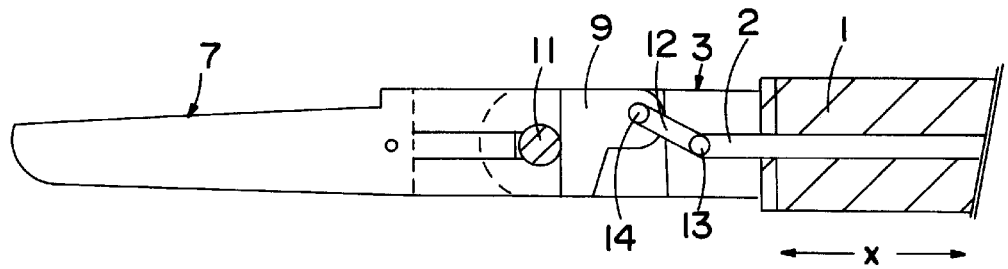
FIG. 3 is a longitudinal section through the front part of the surgical instrument of FIG. 2, along the line III—III.

FIG. 1 shows, for a surgical instrument in accordance with the invention, a front part of an outer tube 1 in which a connecting rod 2 (see FIG. 3) slides. Adjoining the outer tube 1 is a holder 3 which, as shown in FIG. 2, forms a fork with two fork arms 4 and 5, between which the two jaw parts 6 and 7 are inserted. In the present embodiment, both jaw parts 6 and 7 are developed as scissor blades.

For the connecting of the jaw parts 6 and 7 to the holder 3, and for the turnable mounting, there are provided two receivers 8 and 9 which are connected to each other and to the fork arms 4 and 5 via a locking screw 10. Adjoining the locking screw 10 there is a detent pin 13, shown in FIG. 2, around which the receivers 8 and 9 and the jaw parts 6 and 7 are turnably arranged.

The turnability of the receivers 8 and 9 around the detent pin 11 is effected by a movement of the connecting rod 2 in the direction x, in which connection the connecting rod 2 is connected with the receivers 8 and 9 via spreading levers, of which only one spreading lever 12 is shown in FIG. 1. These spreading levers 12, on the one hand, form a pivot pin 13 with the connecting rod 2 and, on the other hand, a pivot joint 14 with the receivers 9 and 8 respectively. Since the spreading levers 12 are arranged towards the outside, the receivers 8 and 9 are turned around the detent pin 11 upon a movement of the connecting rod 2 in the direction x, as a result of which an opening and closing of the jaw parts 6 and 7 takes place. A similar arrangement is described in P 43 32 497.

Each jaw part 6 and 7 has, in accordance with FIGS. 4 and 6, a plate-shaped extension 15, in which a guide slot 16 is formed. Near an end surface 17, a detent hole 18 is arranged in the region of the guide slot 16.

Each receiver 8 and 9 has a support plate 19 and, arranged thereon via a shoulder 20, a nose extension 21 which has a hole 22 to receive the swivel joint 14.

On the support plate 19, there is placed a guide arm 23 which, upon the placing together of jaw parts 6/7 and receivers 8/9, slides into the guide slot 16. In this way, the jaw part 6/7 is guided in direction towards a detent hole 24 which, in the position of use, is passed through by the detent pin 11. By pressure on the jaw part 6 or 7, the detent pin 11 snaps into the detent hole 18 in the region of the guide slot 16, whereby the jaw parts 6/7 are detachably connected to the receiver 8/9.

Jaw parts 6 and 7 are preferably located in a mounting adapter 25 which is preferably so developed that the jaw parts 6 and 7 rest snugly in a recess 26 of a housing 27. The housing 27 is preferably provided on its outer surface with a fluting 28, so that a better transmission of force is effected upon the pushing of the mounting adapter 25 on the two receivers 8 and 9. In this connection, the diameter of the detent hole 18 is reduced to such an extent as compared with the diameter of the detent pin 11 that a pushing-on by means of the mounting adapter 25 is possible, but a pulling-off of the jaw parts 6/7 from the receivers 8/9 by means of only the fingers of the operator or some other person is not possible.

For the better fixing of the jaw parts 6/7 and the handling thereof upon the pushing onto the receivers 8 and 9, holes 29 are furthermore provided in the jaw parts 6/7, through which holes pins, for instance, can be inserted for locking the jaw parts 6/7 in the mounting adapter 25.

For the receiving of the receivers 8/9, the mounting adapter 25 furthermore has a guide channel 30 which leads the receivers 8 and 9 to the jaw parts 6 and 7.

Figure 9:
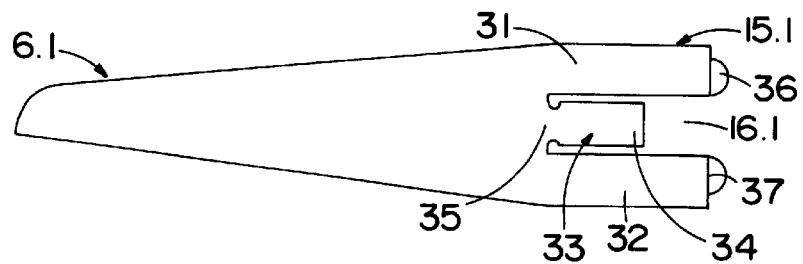
FIG. 9 is a side view of another embodiment of a jaw part in accordance with the invention.
Figure 10:
FIG. 10 is a top view of the jaw part of FIG. 9.

In a further embodiment, shown in FIG. 9, a jaw part 6.1 has an extension 15.1, two strips 31 and 32 forming a guide slot 16.1. Within this guide slot 16.1, there is arranged an elastic tongue 33 which has a detent nose 34. Furthermore, a neck 35 of the tongue 33 is tapered, so that a deflecting of the tongue 33 out of a position of rest, described later, is facilitated.

Figures 11, 12:
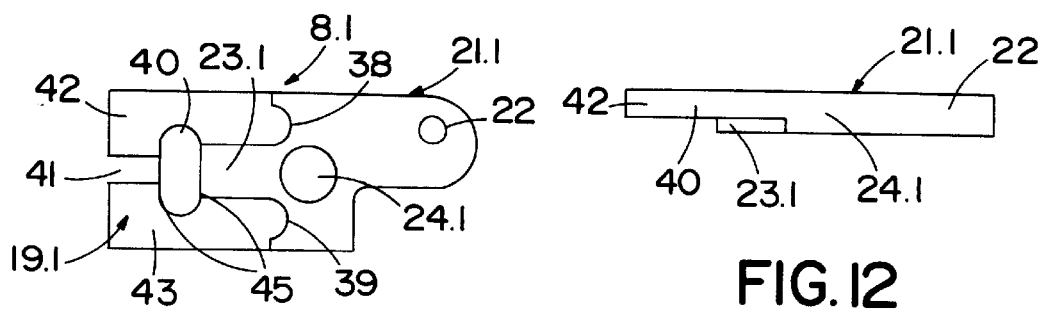
FIG. 11 is a side view of a receiver in accordance with the invention for the jaw part of FIG. 9.
FIG. 12 is a top view of the receiver of FIG. 11.
Figure 13:
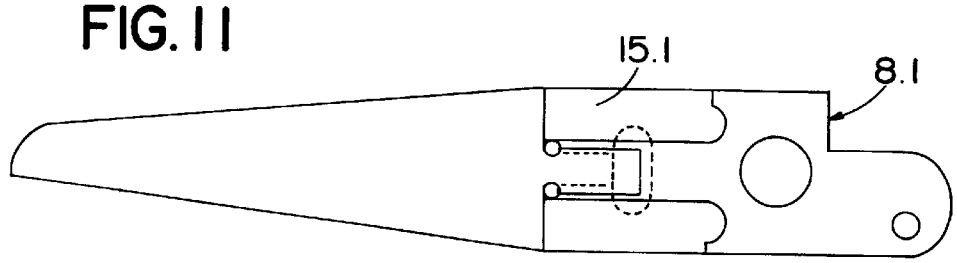
FIG. 13 is a side view of the receiver of FIG. 11 in accordance with the invention, with jaw part in accordance with FIG. 9 engaged.
Figure 14:
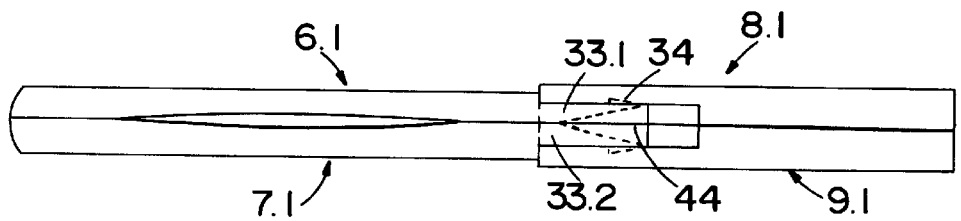
FIG. 14 is a top view of two jaw parts in position of use engaged in the corresponding receivers.

Towards its end, engagement projections 36 and 37 are formed on each strip 31, 32, said projections engaging, in position of use, in corresponding troughs 38 and 39 of a receiver 8.1 (see FIG. 11). The receiver 8.1 has a wider nose extension 21.1 into which, on the one hand, a hole 22 is developed to receive a joint part (not further shown) and, on the other hand, a hole 24.1 to receive a pin.

Adjoining the nose extension 21, there is a support plate 19.1 which is, in part, extended over still by a guide arm 23.1 which extends from the nose extension 21.1. This guide arm 23.1 terminates in front of a hammerhead-shaped transverse slot 40, adjoining which there is a longitudinal slot 41 which, in its turn, separates the support 19 into two support strips 42 and 43.

Upon the insertion of the jaw parts 6.1 and 7.1 into the corresponding receivers 8.1 and 9.1, the extensions 15.1 slide along the support plate 19.1, the elastic tongues 33.1 and 33.2 of the two jaw parts 6.1 and 7.1 respectively being deflected outward with respect to each other. This is made possible in the manner that the tongues 33.1 and 33.2 are cut in wedge shape so that they leave a wedge-shaped free space 44 open between them. Upon the snapping into the transverse slot 40, the detent noses 34 engage behind corresponding undercuts 45 which are formed by the transverse slot 40 upon the transition into the longitudinal slot 41.

This arrangement assures also the possibility of a simple loosening of the jaw parts 6.1 and 7.1 from the corresponding receivers 8.1 and 9.1. It is merely necessary to introduce a corresponding tool into the longitudinal slot 41 or transverse slot 40 which deflects the elastic tongues 33.1 and 33.2 apart from each other, as a result of which the detent noses come loose from the undercuts 45.

Figure 15:
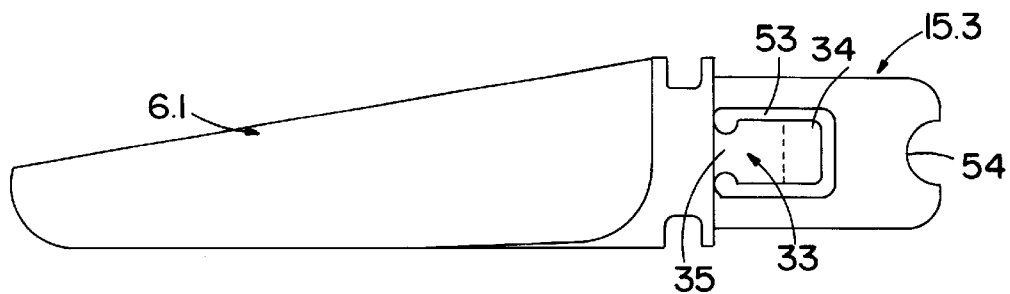
FIG. 15 is a side view of another embodiment of a jaw part in accordance with the invention.
Figure 16:
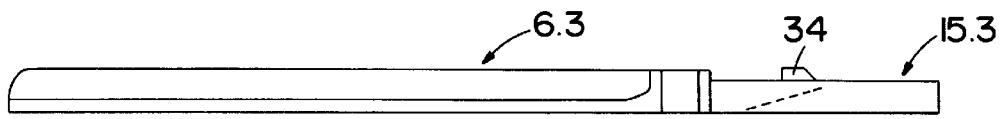
FIG. 16 is a top view of the jaw part of FIG. 15.
Figure 17:
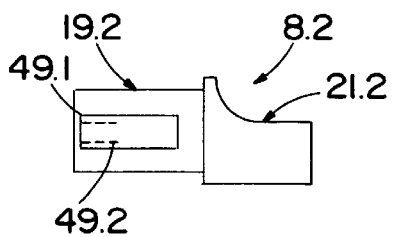
FIG. 17 is a side view of another embodiment of a jaw part in accordance with the invention.
Figure 18:
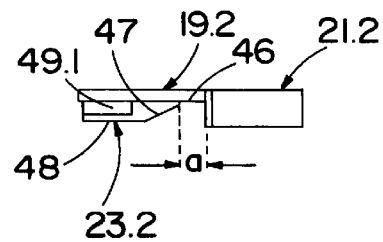
FIG. 18 is a top view of the receiver according to FIG. 17.
Figure 19:
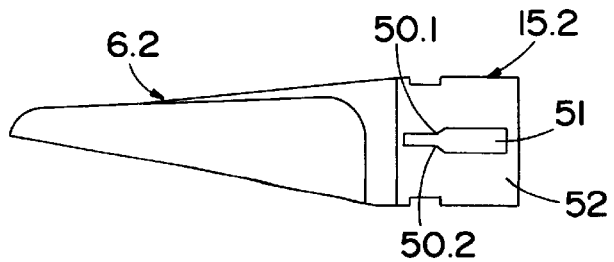
FIG. 19 is a side view of another embodiment of a jaw part in accordance with the invention.

The embodiment of a structural part shown in FIGS. 15 and 16 is similar to that shown in FIGS. 9–14. To be sure, in this case, an extension 15.3 does not have a continuous guide slot, but the elastic tongue 33 is formed from the extension 15.3 by means of a C-shaped slot 53.

Furthermore, the extension 15.3 has on its end a trough-shaped development 54 which cooperates with a corresponding engagement projection (not shown in detail) of a correspondingly shaped receiver.

A receiver 8.2 in accordance with FIGS. 15 and 16 also has a support plate 19.2 which is developed on a nose extension 21.2. On this support plate 19.2 there is a guide arm 23.2 the rear edge 46 of which is at distance a from the nose extension 21.2. From this edge 46, a rising surface 47 rises, it then terminating in a block-like extension 48. In this block-like extension 48 there are developed, from the front, adjoining the support plate 19.2, two grooves 49.1 and 49.2 into which, in position of use, arms 50.1 and 50.2 of a jaw part 6.2 engage. These arms 50.1 and 50.2 are parts of a stepped recess 51 which is formed from a corresponding extension 15.2. In this way, a detent arm 52 is then developed also on the end of the extension 15.2. This detent arm 52 snaps into the region between the edge 46 and the nose extension 21.2 and engages behind the edge 16. At the same time, the jaw part 6.2 is guided with the arms 50.1 and 50.2 in the grooves 49.1 and 49.2 of the guide arm 23, so that, in this way, the jaw part 6.2 is held fast on the receiver 8.2 The advantage of this embodiment of the connection between jaw part 6.2 and the receiver 8.2 is that the jaw part 6.2 can be detached from the receiver 8.2 only when the detent arm 52 or the extension 15.2 is so bent-off that the detent arm 52 can slide onto the rising surface 47. In this case, it is immaterial whether the corresponding guide arms from adjacent recesses are directed towards each other or in opposite directions towards the outside.

We claim:

1. A surgical instrument comprising:
   a support means including a hollow outer tube and a mounting pin;
   at least one jaw part detachably fastened to a receiver, said jaw part being movably mounted on the mounting pin by the receiver;
   a movable element arranged in the outer tube for moving the at least one jaw part about the mounting pin wherein the receiver has an extension which is pivotably connected to the movable element.

2. A surgical instrument according to claim 1, wherein the jaw part has an extension with a guide slot which cooperates with a guide arm on a support plate of the receiver.

3. A surgical instrument according to claim 2, wherein a detent hole is formed in the extension in the region of the slot.

4. A surgical instrument according to claim 3, wherein a detent element is located on the receiver and is associated with the detent hole.

5. A surgical instrument according to claim 4, wherein the detent element is the mounting pin which passes through a hole in the receiver.

6. A surgical instrument according to claim 1, wherein a detent hole is formed in the jaw part.

7. A surgical instrument according to claim 6, wherein a detent element is located on the receiver and is associated with the detent hole.

8. A surgical instrument according to claim 7, wherein the detent element is the mounting pin which passes through a hole in the receiver.

9. A surgical instrument according to claim 1, wherein the receiver is pivotably connected to the movable element by a spreading level.

10. A surgical instrument according to claim 1, wherein the jaw part has a hole for the mounting on the mounting pin.

11. A surgical instrument according to claim 1, wherein the jaw part is provided with an elastic element which, in the position of use, engages behind at least a portion of the receiver.

12. A surgical instrument according to claim 11, wherein the jaw part has an extension from which an elastic tongue having a detent nose is formed via a slot.

13. A surgical instrument according to claim 12, wherein the elastic tongue is connected by a tapered neck with the extension.

14. A surgical instrument according to claim 12, wherein the elastic tongue is connected by a tapered neck with the jaw part.

15. A surgical instrument according to claim 11, wherein a transverse slot in the receiver which forms the portion of the receiver is associated with the detent nose.

16. A surgical instrument according to claim 15, wherein a longitudinal slot adjoins the transverse slot.

17. A surgical instrument according to claim 12, wherein the jaw part has an extension with a stepped recess which cooperates with a guide arm on the receiver.

18. A surgical instrument according to claim 17, wherein the stepped recess has at least one arm which in position of use is introduced into a groove of the guide arm.

19. A surgical instrument according to claim 17, wherein the stepped recess is limited by a detent arm which, in position of use, engages behind an edge of the guide arm.

20. A surgical instrument according to claim 1, wherein the jaw part is received in a mounting adapter.

21. A surgical instrument according to claim 20, wherein the mounting adapter has a housing which has a recess in which the jaw part rests snugly.

22. A surgical instrument according to claim 21, wherein the recess is accessible through a guide channel for the receiver.

* * * * *